United States Patent [19]

Green et al.

[11] Patent Number: 5,364,591
[45] Date of Patent: Nov. 15, 1994

[54] DEVICE FOR MOVING A TARGET-BEARING SOLID THROUGH A LIQUID FOR DETECTION WHILE BEING CONTAINED

[75] Inventors: Nancy F. Green, Pittsford; Thomas J. Cummins, Rochester, both of N.Y.; Fred T. Oakes, Melvern, Pa.

[73] Assignee: Eastman Kodak Company, Rochester, N.Y.

[21] Appl. No.: 891,517

[22] Filed: Jun. 1, 1992

[51] Int. Cl.$^5$ .................. G01N 33/537; G01N 33/546
[52] U.S. Cl. ......................................... 422/58; 422/99; 422/101; 422/102; 435/6; 435/7.5; 435/7.9; 435/7.92; 435/7.94; 435/810; 436/165; 436/518; 436/528; 436/531; 436/532; 436/533; 436/534; 436/538; 436/807; 436/809; 436/810; 530/333; 530/334; 530/338
[58] Field of Search ................. 436/518, 528, 531–534, 436/538, 63, 809, 807, 810, 165; 435/6, 7.5, 7.9, 7.92–7.95, 28, 810, 969, 971; 422/58, 60, 61, 99–102; 530/333, 334, 338

[56] References Cited

U.S. PATENT DOCUMENTS

| | | | |
|---|---|---|---|
| 3,704,206 | 11/1972 | Freake et al. | 195/127 |
| 3,825,410 | 7/1974 | Bagshawe | 422/61 |
| 4,683,195 | 7/1987 | Mullis et al. | 435/6 |
| 4,743,536 | 5/1988 | Evanega et al. | 436/533 |
| 4,786,471 | 11/1988 | Jones et al. | 422/61 |
| 4,921,677 | 5/1990 | Hinckley et al. | 422/103 |
| 4,957,638 | 9/1990 | Smith | 422/101 X |
| 4,962,047 | 10/1990 | Place | 436/518 |
| 4,963,498 | 10/1990 | Hillman et al. | 422/102 X |
| 5,152,965 | 10/1992 | Fisk et al. | 422/102 |
| 5,171,533 | 12/1992 | Fine et al. | 422/101 X |

FOREIGN PATENT DOCUMENTS

| | | | |
|---|---|---|---|
| 381501 | 8/1990 | European Pat. Off. | |
| 8905456 | 6/1989 | WIPO | 422/101 |

OTHER PUBLICATIONS

J. Findlay et al., "Automated Closed-Vessel System for in Vitro Diagnostics Based on Polymerase Chain Reaction," in Clin. Chem. vol. 59, No. 9 (1993) pp. 1927–1933.

F. Braun, "Brave New World Described at San Diego Conference," Clinical Chemistry News, vol. 19, No. 1, Jan. 1993 pp. 1, 2, 10.

*Primary Examiner*—Toni R. Scheiner
*Assistant Examiner*—Christopher L. Chin
*Attorney, Agent, or Firm*—Dana M. Schmidt

[57] ABSTRACT

There are described a device and method for doing confined reactions such as PCR amplification and detection, wherein solids (e.g., beads) used to obtain separation between bound and "free" label reagents, are transferred from region to region, specifically through a wash liquid so as to wash off the "free" label reagent from the solids. Separate chambers have dividers that are overcome by piercing or by liquification, to create passageways for the transfer of the solids. The passageways remain contained within the device.

8 Claims, 4 Drawing Sheets

DEVICE FOR MOVING A TARGET-BEARING SOLID THROUGH A LIQUID FOR DETECTION WHILE BEING CONTAINED

FIELD OF THE INVENTION

This invention relates to devices and methods useful in providing confined reactions such as for PCR amplification and detection.

BACKGROUND OF THE INVENTION

It is known to do PCR amplification and detection using a reaction vessel in which solid particles are fixed and liquid sample and reagents are moved sequentially past the fixed solid particles. Such reaction vessels are described, e.g., in EPA Publication 381,501. Although such vessels work well to confine amplified DNA from leaking out of the vessels and contaminating other test vessels, they do have a slight disadvantage—the liquid solutions must be carefully moved from place to place, without dislodging the fixed solid particles used for detection. As a result, the reaction vessel is carefully constructed in a way that excludes less expensive, simpler constructions. That is, liquid flow and attachment of the "fixed" solids must be maintained so that such solids do not migrate away from their read location.

Similarly, immunoassays are known in which a label reagent attached to a target bound to a solid (and called "bound" reagents) are separated from label reagents associated but unattached with the target (and called "free" reagents). This is done by fixing the solids in the test device and washing off the free reagent by flowing a wash liquid past or around the fixed solids. Typically a medium such as a solid filter is used to separate the bound reagents from the free reagents after the wash step. Examples are indicated in U.S. Pat. No. 4,921,677, which work well for their purpose. However, care is needed to select a filtering medium that, while passing free liquid, will not pass the solids bearings the bound reagent.

Thus, in both the PCR amplification and detection, and in the immunoassays noted above, the technique has been to fix or immobilize the solid particles, and to move the liquid.

There has been a need, therefore, prior to this invention, to provide a detection vessel and method, suitable for PCR amplification and detection while confined, or for immunoassay, that are less difficult to provide and/or less expensive than the currently available vessels and methods.

It was also known in the prior art to pour particulate solids bearing a target, such as for immunoassay, into a detection solution where unbound label reagent is washed off the solids as a bound-free separation. Examples can be found in, e.g., U.S. Pat. No. 4,743,536 to Evanega et al. However, invariably when such solids are poured or flowed into the detection solution, the chamber holding the solids is uncovered to allow the fluid flow. Such uncovering is totally unacceptable as a detection scheme for PCR since the containment needed in PCR amplification becomes lost. Because bulk flow of solids necessitates the opening of sizable channels between the respective compartments, the mere act of providing the bulk flow has in the past been counterproductive to maintaining confinement of PCR reaction products.

What has been desired, therefore, prior to this invention, is a method of flowing bulk solids between confined locations, namely from an amplifying location to a detecting location, without opening up the amplifying location to the atmosphere so as to cause contamination.

SUMMARY OF THE INVENTION

We have devised a device and method that overcome the above-noted problems.

More specifically, in accord with one aspect of the invention, there is provided a device for reacting while contained, a sample target bearing a label reagent, the device comprising a) first means defining a first confined region for attaching the sample target to particulate solids; b) second means defining at least a second confined region containing at least a wash liquid for washing unbound label reagent from some of the solids; c) passage means providing at least one passageway between the first confined location and the second confined location to allow communication of liquid between the confined locations, and d) means for confining and containing the target sample totally within the device when the passageways are opened. The device is improved in that the solids are mobile within the device and the passage means are constructed with a size and distribution sufficient to allow the solids to migrate between the locations and into contact with the liquid label reagent while keeping the target sample totally confined and contained within the device.

In accord with another aspect of the invention, there is provided a process for reacting while contained, particulate solids with a sample target bearing a label reagent, the process comprising a) providing sufficient replicas of the target as to be detectable, b) interacting the detectable target with some particulate solids, and c) detecting label reagent on the target and the solids, all while being confined within a single device during and after step a). The process is improved in that the particulate solids are mobile and the process further includes the step of pouring particulate solids reacted with sample target bearing a liquid reagent, into a wash liquid to remove unbound label reagent, all while the particulate solids and target are confined within the device.

Accordingly, it is an advantageous feature of the invention that no care is needed, in a contained reaction and containment device, in preventing detectable solids from being displaced from a read location, since it is the solids that are mobile and moved, to a fixed liquid, rather than vice-versa.

It is a related advantageous feature that solids bearing both bound and free reagents can be poured into a wash solution for bound/free separation while being retained in a closed, contained environment preventing contamination.

It is a further advantageous feature of the invention that a device and method are provided which avoid processing difficulties inherent in devices that fix solid particles and move liquids relative thereto.

Other advantageous features will become apparent upon reference to the following detailed "Description", when read in light of the attached drawings.

DETAILED DESCRIPTION OF THE INVENTION

Figure 1:
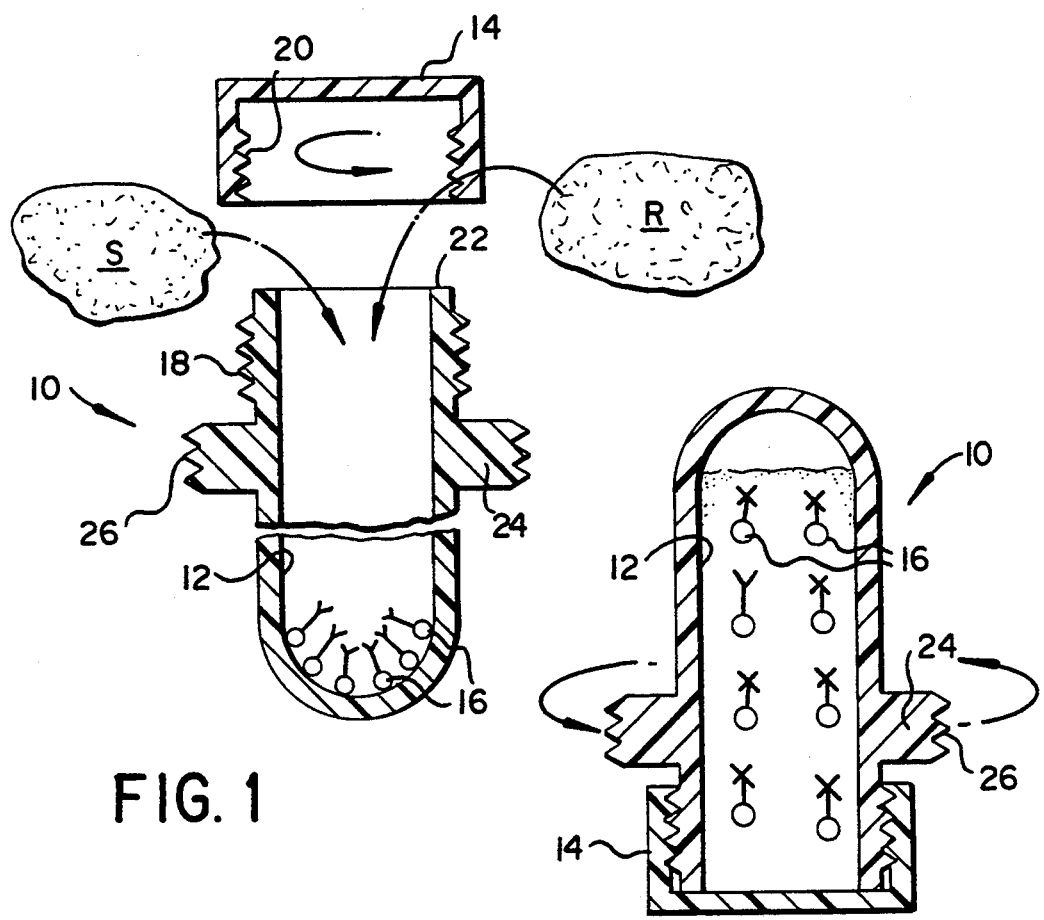
FIG. 1 is an exploded, partially schematic elevational view in section of the first confined region of the device of the invention.

The invention is hereinafter described particularly in connection with certain preferred embodiments, in which PCR amplification and detection takes place within a contained environment to prevent contamination, such as one that is tubular in shape. In addition, it is applicable regardless of whether the reaction scheme is PCR amplification or some other reaction such as an immunoassay, as long as a target sample (e.g., an antibody or antigen), is provided in sufficient quantity as to be detectable, is interacted with both particulate solids and at least a liquid label reagent, in a manner that requires the solids to be mobile so as to move into the label reagent. Also, it is applicable regardless of the shape of the confined locations or the overall device.

As used herein, a "sample target bearing a label reagent" is preferably a replicated oligonucleotide sequence ending in either a label reagent per se, or in biotin that subsequently reacts with an avidin-bearing label reagent. If the sequence ends in a label reagent per se, that label reagent is preferably a fluorescing dye capable of resisting repeated temperature increases of up to 95 degrees C. without losing its ability to fluoresce at a detectable level. Examples of such dyes include fluoresceins or coumarins.

Additionally, "sample target bearing a label reagent" can be an antigen (or antibody) that is complexed with an antibody (or antigen) bearing a label reagent per se, or biotin which subsequently reacts with an avidin-bearing label reagent.

As used herein "label reagent" is a reagent, preferably in solution, capable of directly or indirectly revealing the presence of the sample target. A label reagent is "directly revealing" if it can be detected by stimulating it with outside energy, e.g., if it is a fluorescing moiety that fluoresces when exposed to light. It is "indirectly revealing" if it requires a "detector reagent" also in the device, e.g., if it includes an enzyme that requires a substrate also in the device, to produce a color for example.

Also as used herein, "interacting the target with both particulate solids and at least a liquid label reagent" means either sequentially as usually occurs at two separate reactive sites on the sample target, e.g., an antigen with two epitope sites each reactive sequentially with an antibody on a solid, and then with a labeled antibody; or simultaneously such as occurs when a target antigen interacts with a soluble labeled antigen competitively for an antibody on a solid.

Particularly useful label reagents comprise enzymes attached to strepavidin, such as peroxidases and particularly horseradish peroxidase. When the latter enzyme is used, a useful substrate is $H_2O_2$ and a triarylimidazole dye such as those described in Babb et al U.S. Pat. No. 4,670,386 issued Jun. 2, 1987, and Bruschi U.S. Pat. No. 4,089,747 issued May 16, 1978.

"Particulate solids" as used herein refer to any solids to which the target can be readily bound, preferably those that are relatively small particulates, e.g., those having as their maximum dimension, a value no greater than about 300 $\mu$m. Highly preferred are beads of polystyrene dimensioned to be about 0.1–100 $\mu$m.

Referring now to the features of the invention in combination, each of the features a)–d) of the device set forth in the Summary above is already known by itself. That is, they appear generically in the aforesaid EPA 381,501, wherein however the particulate solids are fixed and the liquid reagents flow over those solids.

Thus, a device constructed in accordance with the invention includes, FIG. 1, a first confined region 10 provided by a chamber 12 with a removable sealing cap 14, that is applied to seal the device after all the reagents R and sample S needed for PCR amplification are in place. Pre-included in chamber 12 are beads 16 bearing a linking group shown as a "Y", which group is preferably an oligonucleotide probe designed to anneal to the target DNA that is to be amplified in chamber 12. Both the sample S and all the needed reagents for amplification are added to the device and cap 14 is sealed. Any sealing means can be used, but preferably they comprise a male and female thread 18, 20, with preferably the male thread being on the top portion 22 of chamber 12.

Chamber 12 has on its outside, confining means for allowing it to securely attach to the remaining portion(s) 30 of the device, in a manner that allows the contents of chamber 12 to be poured into portion 30 while keeping all liquids confined within the device. Preferably the confining means comprise a protruding lip 24 on which is mounted male screw threads 26.

Reagents R preferably also include a primer for the targeted nucleic acid sequence to which is attached a fluorescing label.

Thereafter, PCR amplification occurs in chamber 12 using known temperature cycling, to provide sufficient labeled replicas of the targeted nucleic acid sequence, such as DNA, as can be readily detected in other portions of the device and method. To ensure the amplification is not unduly hindered by premature annealing to the beads, the probe on the bead is selected to have a lower $T_m$, that is, a lower melt temperature than the $T_m$ of the amplification primers, as is well-known.

Figure 2:
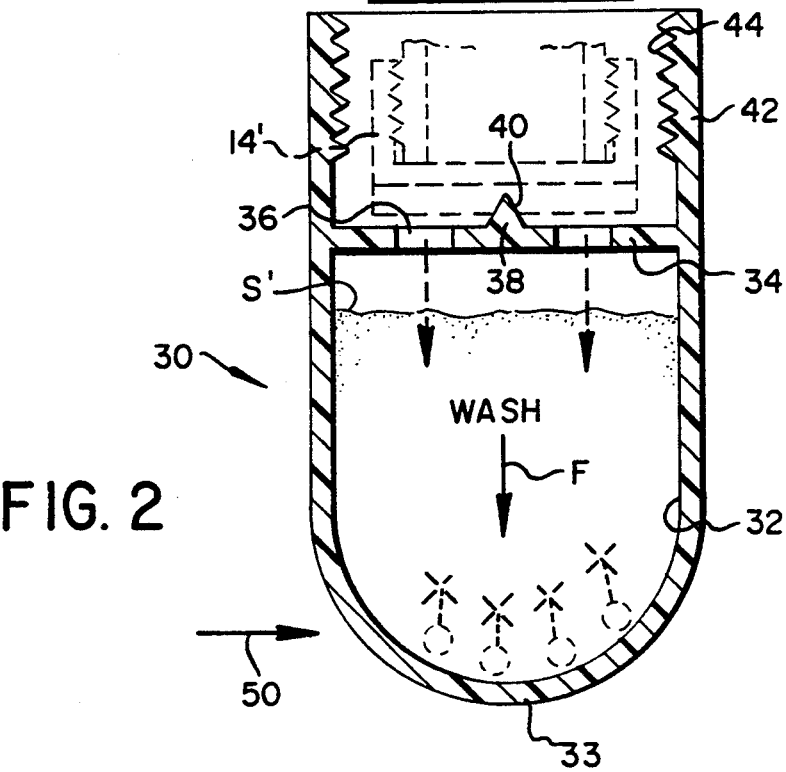
FIG. 2 is a view similar to that of FIG. 1 but also illustrating the second confined region, in its cooperation with the first confined region, and also the means for confining the target during the processing of the invention.

The result is that some beads 16 have, FIG. 2, targeted nucleic acid sequence bound to them, as shown by the "X"s.

At this point, beads 16 of chamber 12 also bear on them, loosely attached, unannealed primers bearing the fluorescing medium. Some of the beads may have only such loosely attached, unannealed primers.

Turning next to FIG. 2, the other portion of the device comprises a second confined region 30, including a chamber 32 having a bottom wall 33, covered by cover 34 apertured at 36. Center portion 38 of cover 34 has a piercing prong 40 capable of bursting through cover 14 on contact. Rising above cover 34 is a sleeve 42 that is provided with female threads 44 for engagement with threads 26 of chamber 12. When threads 44 and 26 are initially engaged, cover 14 is spaced away from contact with prong 40, as shown by the raised phantom 14' position of the cover. However, as chamber 12 is further screwed into sleeve 42, prong 40 penetrates cover 14 sufficiently to provide a passageway for solids 16 and any reagents thereon.

The liquid content of chamber 32 is at least a wash liquid. The effect of the wash liquid is to wash off the beads, as they fall by reason of force "F" to the bottom wall 33, any loosely "attached" unannealed labeled primer. Such washed-off primer stays near the surface "S'" of the wash liquid. Force "F" can be supplied either as gravity or as a centrifugal force.

What then reaches bottom wall 33 is only the beads and label reagent that is part of the targeted DNA due to the amplification process (as annealed to the beads). The label reagent, by reason of its fluorescing capability, can then be detected by emitting light of the appropriate wavelengths, at the bottom region of chamber 32, arrow 50.

Thus, amplification, wash and detection all occur within a sealed, contained device, even when the transfer mechanism is one of transfer of solids from first region 10 to second region 30, and not just liquids.

As noted above, the label reagent need not be a fluorescing moiety, but can instead comprise an enzyme that cooperates with a substrate to produce a detectable color. In that case, a 3-chambered device is preferred, FIGS. 3 and 4. Parts similar to those previously described bear the same reference numeral, to which the distinguishing suffix "A" is appended.

Thus, the device comprises two cooperating confining portions 10A and 30A, screw-attached by mating threads 26A and 44A to allow piercing of cover 14A as before. (Cover 14A can be screw-attached as in the previous embodiment.) However, an additional confined region 70 is added by extending the walls of chamber 32A and inserting region 70 above a barrier means 74, to create a third chamber 72 located between barrier means 74 and cover 34A.

In this construction, the liquid within chamber 72 comprises an enzyme chemically modified to react with targeted nucleic acid sequences produced in chamber 12A. (If immunoassays are involved, the chemical modification of the enzyme allows it to react with an antibody complexed to the targeted antigen.) Preferred is the use of avidin chemically reacted with the enzyme, in which case the targeted nucleic acid sequences end in biotin. A highly preferred example of the liquid in region 70 is strepavidin horseradish peroxidase.

If the enzyme is a peroxidase, then $H_2O_2$ is also included in chamber 72 in portion 30A.

Figure 3:
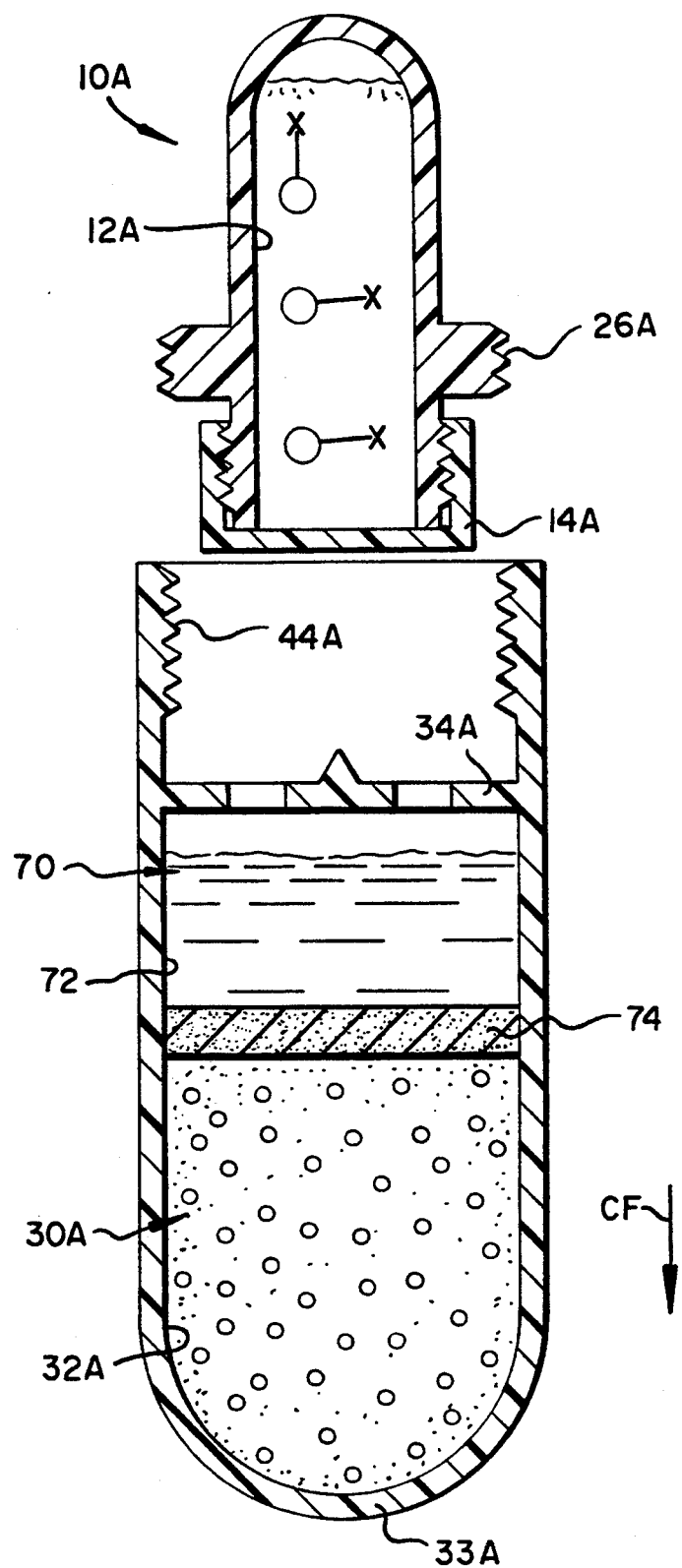
FIG. 3 is a view similar to that of FIG. 2 but illustrating an alternate embodiment of the invention prior to providing a passageway through the confinements of the various confined regions.
Figure 4:
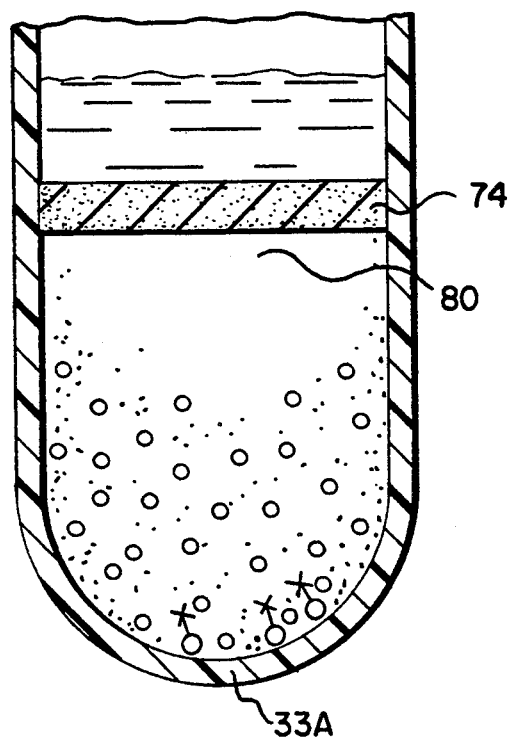
FIG. 4 is a fragmentary elevational view in section of only the lower half of the device, following the opening of passageways in the confinements shown in FIG. 3.

A variety of barrier means 74 are useful. In the embodiment of FIGS. 3 and 4, barrier means 74 preferably are liquifiable under the influence of either a temperature change or of centrifugal force. Examples of the former include a wax that liquifies when heated to a temperature less than that which deactivates the enzyme, e.g., a temperature less than 60° C. Paraffin is a preferred example.

Examples of a barrier means that liquifies under centrifugal force include thixotropic gels that will allow passage of the beads at a high centrifugal force "CF", for example, a force of at least 10,000 G's. A preferred example of such a gel includes the gel available in tubes sold by Sarstedt Corp; under the tradename "Gel Monovette", usually comprising silica and a polyester.

In this embodiment, the liquid content of confined region 30A comprises a substrate for the enzyme of chamber 72, for example, a leuco dye in aqueous solution. Thus, the liquid content provides two functions: it provides the washing of the beads as they move past barrier means 74, FIG. 4, to remove loosely "attached" enzyme that is not reacted by the avidin-biotin linkage to the beads, and it provides the substrate for the enzyme.

The beads that collect on bottom wall 33 are then detected by their color change. Any color change created at the top portion 80 of chamber 30A due to the washed-off loose enzyme, can be readily spatially distinguished from the color change of the beads at wall 33A.

It is not essential that barrier means 74 be liquifiable, or indeed, be anything other than a rigid structure. Thus, FIG. 5, it can be a wall structure cutting off chamber 72 from everything below, including chamber 32A. Parts similar to those previously described bear the same reference numeral to which the distinguishing suffix "B" has been appended.

Figure 5:
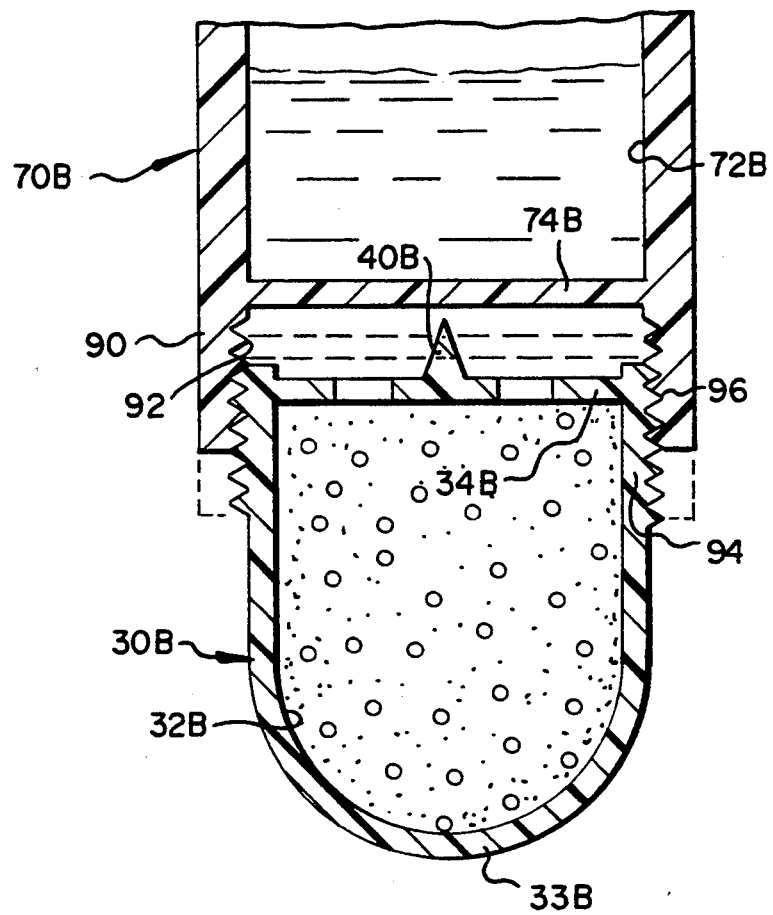
FIG. 5 is a view similar to that of the lower half of FIG. 3, but illustrating yet another alternate embodiment.

As shown in FIG. 5, the device is identical to those previously described, insofar as middle region 70B, its chamber 72B, and the first confined region (not shown) are concerned, except that barrier means 74B now comprises a thin wall that is an extension of the walls of chamber 72B, so as to close off access out of that chamber. In addition, a skirt 90 extends down below barrier means 74B, which is internally threaded at 92. Third confined region 30B then comprises a chamber 32B with a bottom wall 33B as before, except that at the top 94 of region 30B, there are disposed an apertured cover 34B constructed substantially identically as cover 34A, and external threads 96 that mate with threads 92. Thus, prong 40B acts to break through barrier 74B simply by screwing chamber 32B farther into skirt 90. In either position, the threaded engagement of skirt 90 by threads 96 ensures that no leakage can occur out of the device. When prong 40B does burst through barrier wall 74B, the solids (beads) in chamber 72B then flow down into chamber 32B as before, to wash off unbound label reagent and to react bound label reagent to produce colored beads at the bottom, adjacent to wall 33B.

EXAMPLES

The following non-limiting examples further illustrate the invention:

Example 1

To show that the barrier means and washing step function as described above, synthetic DNA samples were prepared at concentrations from 200 pmoles down to 0 pmoles. The DNA was suspended in a tris(hydroxymethyl)-aminomethaneethylenediaminetetraacetic acid buffer, then diluted 1:30 in a high salt buffer.

DNA probes were covalently attached to beads of poly[styrene-co-3-(p-vinylbenzylthio)propionic acid] (weight ratio 95:5) (approximately 1 micron). The beads were suspended at 0.24% solids and 6% a diatomaceous earth under the tradename of "Celite", manufactured by Johns-Manville Products Corporation in a streptavidin-HRP (SA-HRP) solution.

Microcentrifuge tubes were prepared containing a bottom layer of 100 μl 10.5% agarose/4% Sodium chloride in 4,5-bis(4-dimethylaminophenyl)-2-(4-hydroxy-3,5-dimethoxyphenyl)imidazole leuco dye solution. A second layer contained 500 μl of 0.5% agarose/2% sodium chloride in water.

200 μl of a DNA sample was denatured at 95° C. for 5 minutes. 100 μl of the bead/Celite/SA-HRP was added to the sample. The sample was vortexed for 5 seconds, then 100 μl of the sample was added to the prepared microcentrifuge tube to simulate the embodiment of FIG. 3. (No cover 14 or 14A was used.)

The tube was centrifuged for 5 minutes at 14,000 rpm, then the color of the pellet was observed.

Figure 6:
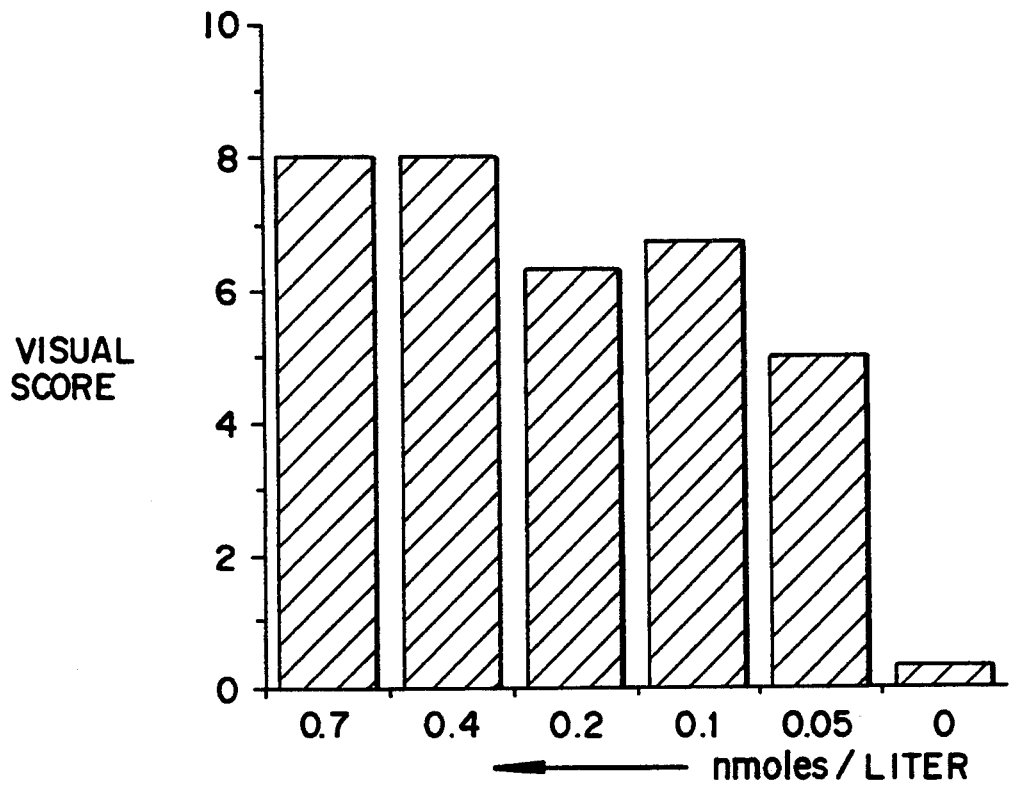
FIGS. 6 and 7 are each a plot or graph depicting assay sensitivity.

As seen in the graph of FIG. 6 this method detects as low as 0.05 nmoles/L.

Example 2

The procedure of Example 1 was repeated, except that the suspension of the beads was at 1.2% solids, and the diatomaceous earth was replaced with 1% Zonyl FSN TM, a non-ionic, fluorinated surfactant available from dupont de Nemours. The tubes were used in Sarstedt "microvette SCB 1000" gel tubes, and agarose was left out of the leuco dye solution. The sole barrier means (74 in FIG. 3) was the Sarstedt gel. The concentration of NaCl was boosted to 15%. The processing occurred as follows: the tubes so prepared were centrifuged for 1 minute at 14,000 rpm and rinsed in deionized and distilled, microfiltered water, only for the purpose of locating the leuco dye solution below the barrier means. Then 50 µl of a Streptavidin-HRP (SA-HRP) solution with 5% Celite was layered on the gel.

307 µl of a DNA sample was denatured at 95° C. for 5 minutes. 34 µl of the bead/Zonyl FSN was added to the sample. The sample incubated at 42° C. for 5 minutes. Then 100 µl of the sample was added to the prepared tube.

The tube was centrifuged 5 minutes at 14,000 rpm, then the color of the pellet was observed.

Figure 7:
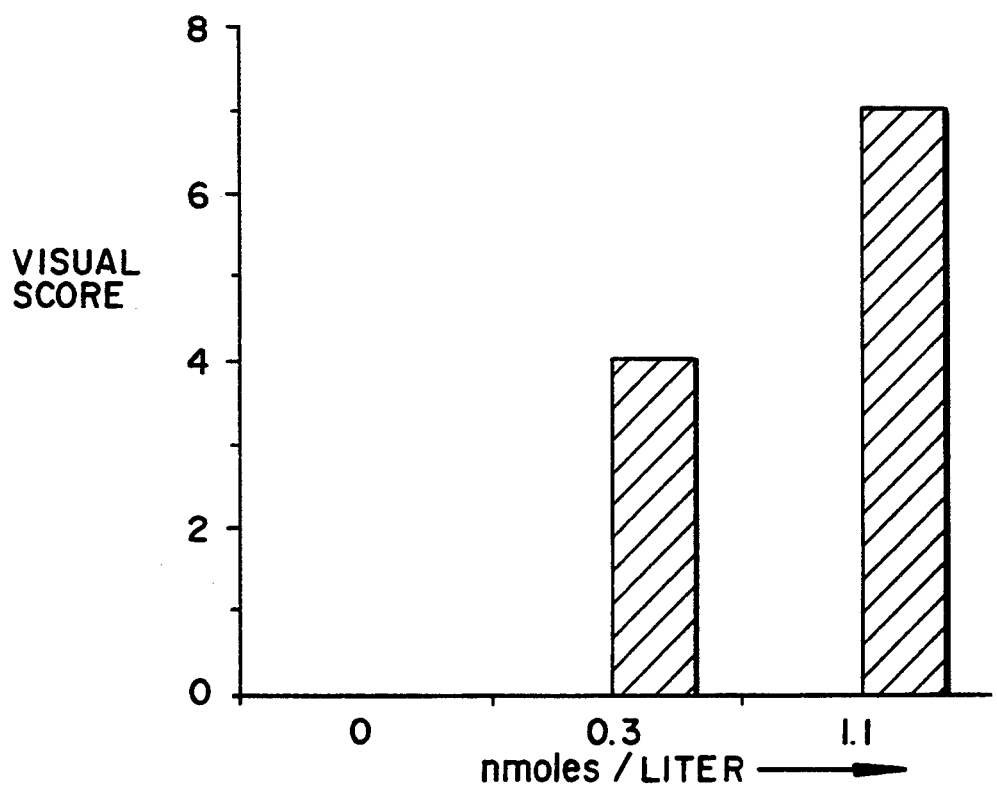

As seen in the graph of FIG. 7, this method detects as low as 0.3 nmoles/L sample and no color is observed when no sample is present.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A device for reacting while contained, a sample target with (i) a mobilizable particulate solid phase reagent having immobilized thereon a specific binding partner capable of specifically binding the sample target and (ii) a label reagent comprising a detectable label conjugated to a second specific binding partner capable of specifically binding the sample target in order to bind the label reagent to the mobilizable particulate solid phase reagent in an amount indicative of the sample target, the device comprising:

a) a first confined chamber comprising said mobilizable particulate solid phase reagent, said label reagent, and a pierceable cover capable of completely sealing said first confined chamber;

b) at least a second confined chamber containing at least a wash liquid for washing any unbound label reagent from said mobilizable particulate solid phase reagent, wherein said second confined chamber further comprises an aperture and a piercing means; and c) confining means for confining and containing said sample target totally within said device when a sealed passageway is opened between said first and second confined chambers, said confining means comprising threaded means for removably holding together said first and second chambers in two spaced-apart orientations, one orientation being effective to keep said piercing means out of contact with said pierceable cover and the other of said orientations being effective to pierce said pierceable cover with said piercing means;

wherein said sealed passageway is formed when said pierceable cover is pierced by said piercing means when said confining means is in said second orientation and said mobilizable solid phase reagent moves from said first confined chamber to at least said second confined chamber and said wash liquid washes off any unbound label reagent.

2. A device for reacting while contained, a sample target bearing biotin, with (i) a mobilizable particulate solid phase reagent having immobilized thereon a specific binding partner capable of specifically binding the sample target and (ii) a label reagent comprising a detectable label conjugated to avidin in order to bind the label reagent to the mobilizable particulate solid phase reagent in an amount indicative of the sample target, the device comprising:

a) a first confined chamber comprising said mobilizable particulate solid phase reagent and a pierceable cover capable of completely sealing said first confined chamber;

b) a second confined chamber containing said label reagent to react with biotin on the sample target, wherein said second confined chamber further comprises an aperture and a piercing means;

c) confining means for confining and containing said sample target totally within said device when a sealed passageway is opened between said first and second confined chambers, said confining means comprising threaded means for removably holding together said first and second chambers in two spaced-apart orientations, one orientation being effective to keep said piercing means out of contact with said pierceable cover and the other of said orientations being effective to pierce sand pierceable cover with said piercing means;

wherein said sealed passageway is formed when said pierceable cover is pierced by said piercing means when said confining means is in said second orientation and said mobilizable solid phase reagent moves from said first confined chamber to at least said second confined chamber; and a third confined chamber containing a wash liquid for washing any unbound label reagent from said mobilizable particulate solid phase reagent, wherein said third confined chamber is temporarily separated from said second confined chamber by a separating means.

3. A device for reacting while contained, a sample target with (i) a mobilizable particulate solid phase reagent having immobilized thereon a specific binding partner capable of specifically binding the sample target and (ii) a label reagent comprising biotin conjugated to a second specific binding partner capable of specifically binding the sample target in order to bind the label reagent to the mobilizable particulate solid phase reagent in an amount indicative of the sample target, the device comprising:

a) a first confined chamber comprising said mobilizable particulate solid phase reagent, said label reagent, and a pierceable cover capable of completely sealing said first confined chamber;

b) a second confined chamber containing a liquid comprising avidin conjugated to a detectable label, wherein said second confined chamber further comprises an aperture and a piercing means;

c) confining means for confining and containing said sample target totally within said device when a sealed passageway is opened between said first and second confined chambers, said confining means comprising threaded means for removably holding together said first and second chambers in two spaced-apart orientations, one orientation being effective to keep said piercing means out of contact with said pierceable cover and the other of said orientations being effective to pierce said pierceable cover with said piercing means;

wherein said sealed passageway is formed when said pierceable cover is pierced by said piercing means when said confining means is in said second orientation and said mobilizable solid phase reagent moves from said first confined chamber to at least said second confined chamber; and a third confined chamber containing a wash liquid for washing any unbound label reagent from said mobilizable particulate solid phase reagent, wherein said third confined chamber is temporarily separated from said second confined chamber by a separating means.

4. A device as defined in claims 2 or 3, wherein said second chamber includes a pierceable wall surface effective to confine all substances within said second chamber until pierced, said third chamber having an apertured cover and means for piercing said pierceable wall surface, said device further including threaded means for removably holding together said second and third chambers in two spaced-apart orientations, one orientation being effective to keep said piercing means out of contact with said pierceable wall surface and the other of said orientations being effective to pierce said pierceable wall surface.

5. A device as defined in claims 2 or 3, wherein said wash liquid in said third chamber further comprises a detector reagent reactive with said detectable label reagent to directly reveal the presence of said target, and said separating means being capable of change to create a passageway therethrough to provide flow of particulate solids between said second and third confined chambers.

6. A device as defined in claim 5, wherein said separating means is a barrier layer of a material which liquifies under either a temperature change or a centrifugal force.

7. A device as defined in claim 6, wherein said barrier layer comprises a wax layer that liquifies when heated and wherein said label reagent is thermally stable to at least the temperature of liquification of said wax.

8. A device as defined in claim 6, wherein said barrier layer comprises a thixotropic gel layer effective to pass solid particles having maximum dimensions no larger than 300 $\mu$m, when a centrifugal force of at least 10,000 G's is applied.

* * * * *